(12) United States Patent
Akaki

(10) Patent No.: US 9,259,207 B2
(45) Date of Patent: Feb. 16, 2016

(54) ULTRASOUND DIAGNOSTIC APPARATUS AND ULTRASOUND SIGNAL ANALYZING METHOD

(75) Inventor: Kazuya Akaki, Nasushiobara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 531 days.

(21) Appl. No.: 11/218,639

(22) Filed: Sep. 6, 2005

(65) Prior Publication Data

US 2006/0052705 A1 Mar. 9, 2006

(30) Foreign Application Priority Data

Sep. 6, 2004 (JP) ................................. 2004-258468

(51) Int. Cl.
*A61B 8/06* (2006.01)
*A61B 8/13* (2006.01)
*A61B 8/08* (2006.01)

(52) U.S. Cl.
CPC ... *A61B 8/13* (2013.01); *A61B 8/06* (2013.01); *A61B 8/488* (2013.01)

(58) Field of Classification Search
CPC ....... A61B 8/488; A61B 8/06; G01S 7/52073
USPC ................................................. 600/407–480
See application file for complete search history.

(56) References Cited

U.S. PATENT DOCUMENTS

| 3,663,932 | A | * | 5/1972 | Mount et al. ..................... 367/90 |
| 4,141,347 | A | * | 2/1979 | Green et al. .................. 600/441 |
| 5,014,710 | A | * | 5/1991 | Maslak et al. ................. 600/441 |
| 5,212,490 | A | * | 5/1993 | Nelson et al. .................. 327/185 |
| 5,287,753 | A | * | 2/1994 | Routh et al. ............... 73/861.25 |
| 6,068,598 | A | * | 5/2000 | Pan et al. ........................ 600/453 |
| 6,663,566 | B2 | * | 12/2003 | Pan et al. ........................ 600/454 |
| 6,679,847 | B1 | * | 1/2004 | Robinson et al. ............. 600/447 |
| 2003/0100833 | A1 | * | 5/2003 | He et al. ......................... 600/446 |
| 2003/0158484 | A1 | * | 8/2003 | Pan et al. ........................ 600/453 |
| 2006/0287600 | A1 | * | 12/2006 | McEowen ..................... 600/481 |

FOREIGN PATENT DOCUMENTS

| JP | 6-133972 | | 5/1994 | |
| JP | 7-241290 A | | 9/1995 | |
| JP | 8308843 | * | 11/1996 | ............... A61B 8/06 |
| JP | 2003-245279 A | | 9/2003 | |

OTHER PUBLICATIONS

Japanese Office Action issued on Mar. 8, 2011 in corresponding Japanese Application No. 2005-232359 (with an English Translation).

* cited by examiner

*Primary Examiner* — Amanda Lauritzen Moher
*Assistant Examiner* — Serkan Akar
(74) *Attorney, Agent, or Firm* — Oblon, McClelland, Maier & Neustadt, L.L.P.

(57) ABSTRACT

In quantitative analysis using blood flow velocity measurement and the like, whether to select the forward direction or reverse direction is determined in accordance with the positional relationship between a baseline for controlling the display scale of a Doppler waveform and a reference line which can be arbitrarily set by an operator. The determination is executed at one of the stages of selecting a tracing direction by an automatic tracing process, selecting an approximate Doppler waveform as an analysis target, and selecting an analysis result as a display target.

20 Claims, 12 Drawing Sheets

ULTRASOUND DIAGNOSTIC APPARATUS AND ULTRASOUND SIGNAL ANALYZING METHOD

CROSS-REFERENCE TO RELATED APPLICATIONS

This application is based upon and claims the benefit of priority from prior Japanese Patent Application No. 2004-258468, filed Sep. 6, 2004, the entire contents of which are incorporated herein by reference.

BACKGROUND OF THE INVENTION

1. Field of the Invention

The present invention relates to an ultrasound diagnostic apparatus and ultrasound signal analyzing method which measure a blood flow velocity and the like and provide information effective for medical diagnosis.

2. Description of the Related Art

An ultrasound diagnostic apparatus is a medical image device which noninvasively obtains a tomographic image of soft tissue in a living body from the body surface by the ultrasound pulse reflecting method. This ultrasound diagnostic apparatus has advantages of being smaller in size, more inexpensive, and safer because of no exposure to X-rays and the like than other medical image devices, and of being capable of blood flow imaging, and hence is widely used in a cardiac department, abdominal department, urological department, obstetrics and gynecology, and the like.

This ultrasound diagnostic apparatus can provide not only an ultrasound image generated on the basis of an acquired echo signal but also clinical information obtained by quantitative analysis using the echo signal. Quantitative analysis includes a type associated with morphological information and a type associated with blood flow information. The latter type, in particular, typically uses blood flow indexes such as a PI (Pulsatility Index), RI (Resistance Index), S/D (Systelic Velocity/Diastoric Velocity), and the like calculated by using Doppler waveforms. For example, these blood flow indexes are acquired in the following manner.

First of all, a Doppler waveform acquired by a Doppler mode is displayed as shown in FIG. 1. An operator determines a display scale for a Doppler waveform by manually moving a baseline $L_b$ indicating velocity 0 to an arbitrary position. When a display scale is determined, an automatic tracing process for extracting an approximate shape of the Doppler waveform in a predetermined direction (the positive direction of velocity in FIG. 2). Quantitative indexes for a blood flow such as a PI, RI, and S/D are calculated by using an approximate waveform Wa like that shown in FIG. 2 which is extracted in this manner.

In the conventional ultrasound diagnostic apparatus, a direction (tracing direction) in which an approximate waveform is to be extracted by an automatic tracing process must be artificially set before automatic tracing. If, therefore, the operator forgets to set a tracing direction, an automatic tracing process is executed in a previously or initially set tracing direction.

BRIEF SUMMARY OF THE INVENTION

The previously or initially set tracing direction is not, however, suitable for an automatic tracing process to be currently executed. More specifically, for example, main components of the Doppler waveform acquired by the Doppler mode sometime appear on the lower side of a baseline Lb as shown in FIG. 3 depending on the blood flow direction. In such a case, if the operator forgets to set a tracing direction and the previous tracing direction setting (e.g., the tracing direction setting in FIG. 2) has been executed, the approximate waveform Wa like that shown in FIG. 4 is extracted. Therefore, the operator needs to check a tracing direction setting for every automatic tracing process, resulting in poor operability. In addition, if an automatic tracing process is performed in a wrong tracing direction, the operator is forced to redo an automatic tracing process. This reduces the efficiency of the overall work, and increases the mental and physical strains on the operator and subject.

The present invention has been made in consideration of the above situation, and has as its object to provide an ultrasound diagnostic apparatus and ultrasound signal analyzing method which can properly and automatically set a tracing direction in an automatic tracing process used for quantitative analysis by the ultrasound diagnostic apparatus.

According to an aspect of the present invention, there is provided an ultrasound diagnostic apparatus comprising a Doppler information generating unit which generates blood flow Doppler information concerning at least one of a first direction and second direction on the basis of an echo signal obtained by an ultrasound wave transmitted to a subject to be examined on the basis of a supplied driving signal, an approximate information generating unit which generates approximate information of the blood flow Doppler information, an analyzing unit which acquires an analysis result by executing analysis using the approximate information, a determining unit which determines, on the basis of a position of a baseline of the Doppler information, whether the first direction or the second direction is a target direction, and a display unit which displays the analysis result.

According to another aspect of the present invention, there is provided an ultrasound signal analyzing method comprising generating blood flow Doppler information concerning at least one of a first direction and second direction on the basis of an echo signal obtained by an ultrasound wave transmitted to a subject to be examined on the basis of a supplied driving signal, generating approximate information of the blood flow Doppler information, acquiring an analysis result by executing analysis using the approximate information, determining, on the basis of a position of a baseline of the Doppler information, whether the first direction or the second direction is a target direction, and displaying the analysis result.

DETAILED DESCRIPTION OF THE INVENTION

Figure 1:
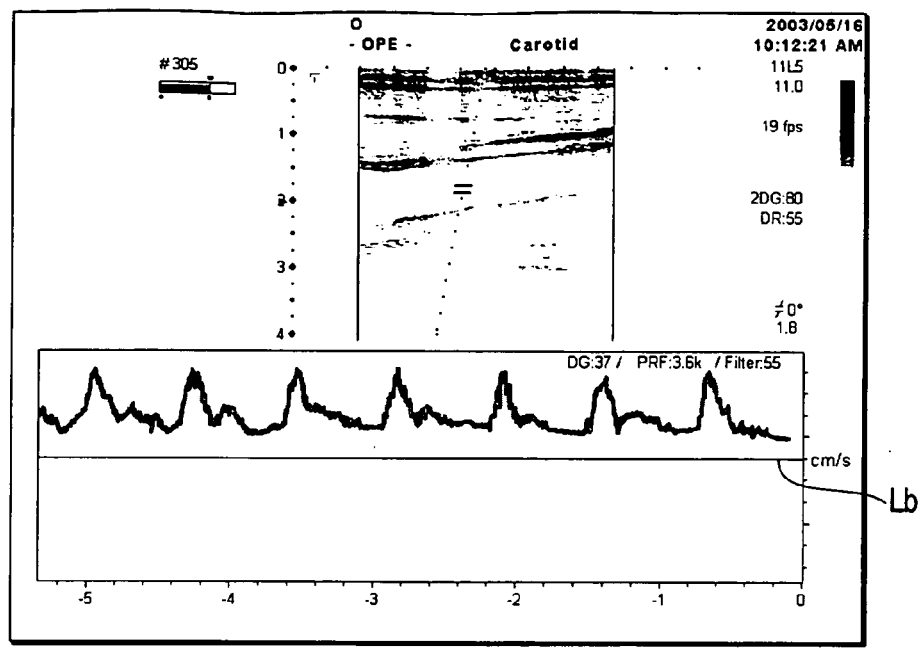
FIG. 1 is a view for explaining a conventional automatic tracing process.
Figure 2:
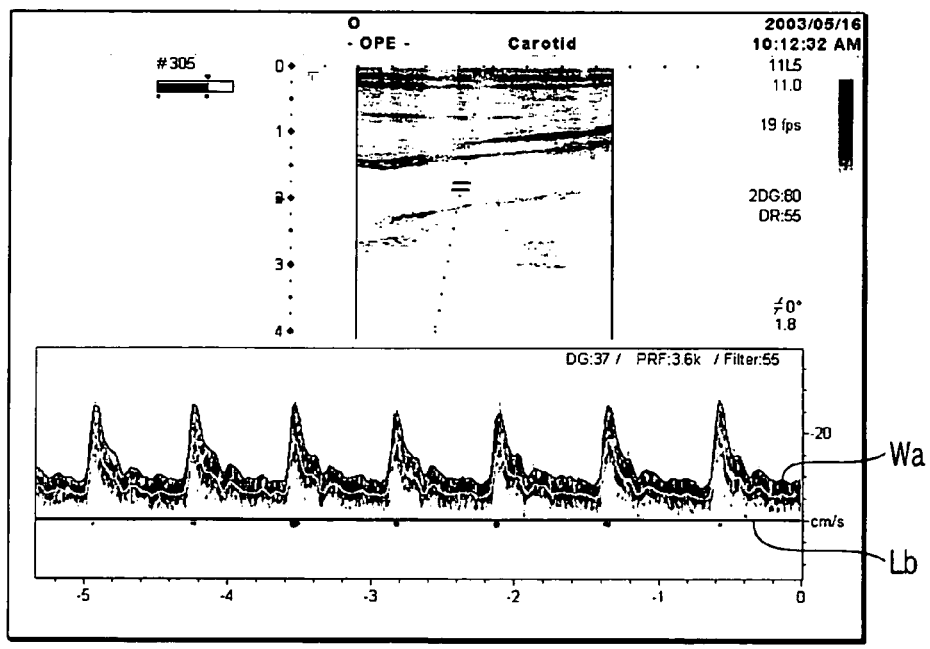
FIG. 2 is a view for explaining a conventional automatic tracing process.
Figure 3:
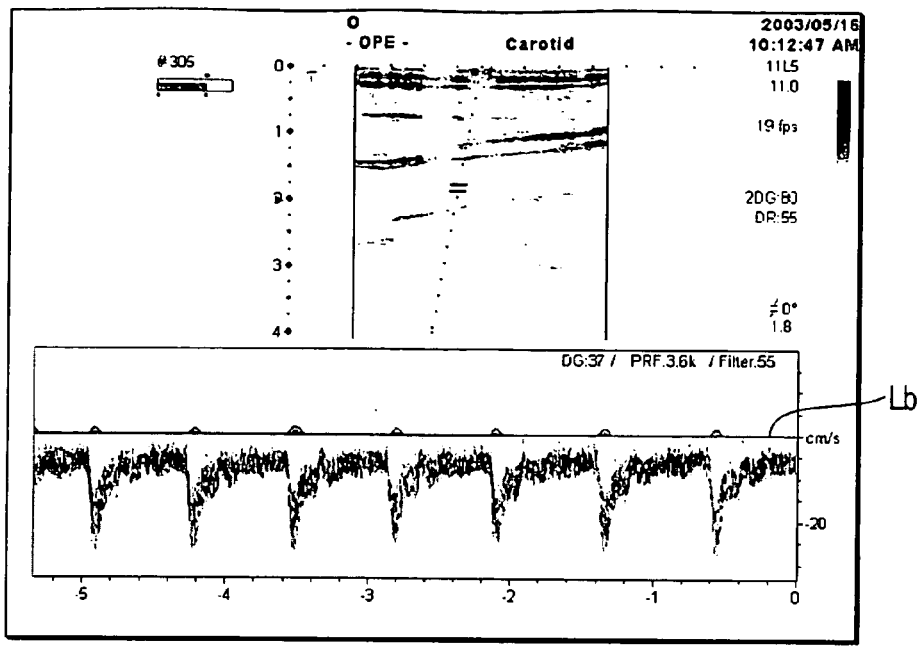
FIG. 3 is a view for explaining a conventional automatic tracing process.
Figure 4:
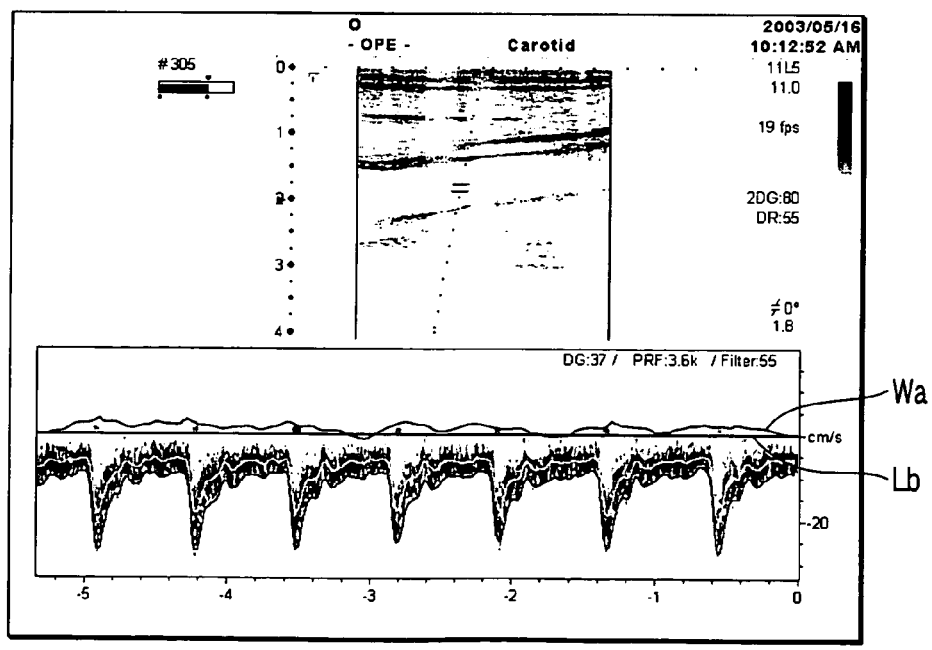
FIG. 4 is a view for explaining a conventional automatic tracing process.

An embodiment of the present invention will be described below with reference to the views of the accompanying drawing. Note that the same reference numerals denote constituent elements having substantially the same functions and arrangements, and a repetitive description will be made only when required.

Figure 5:
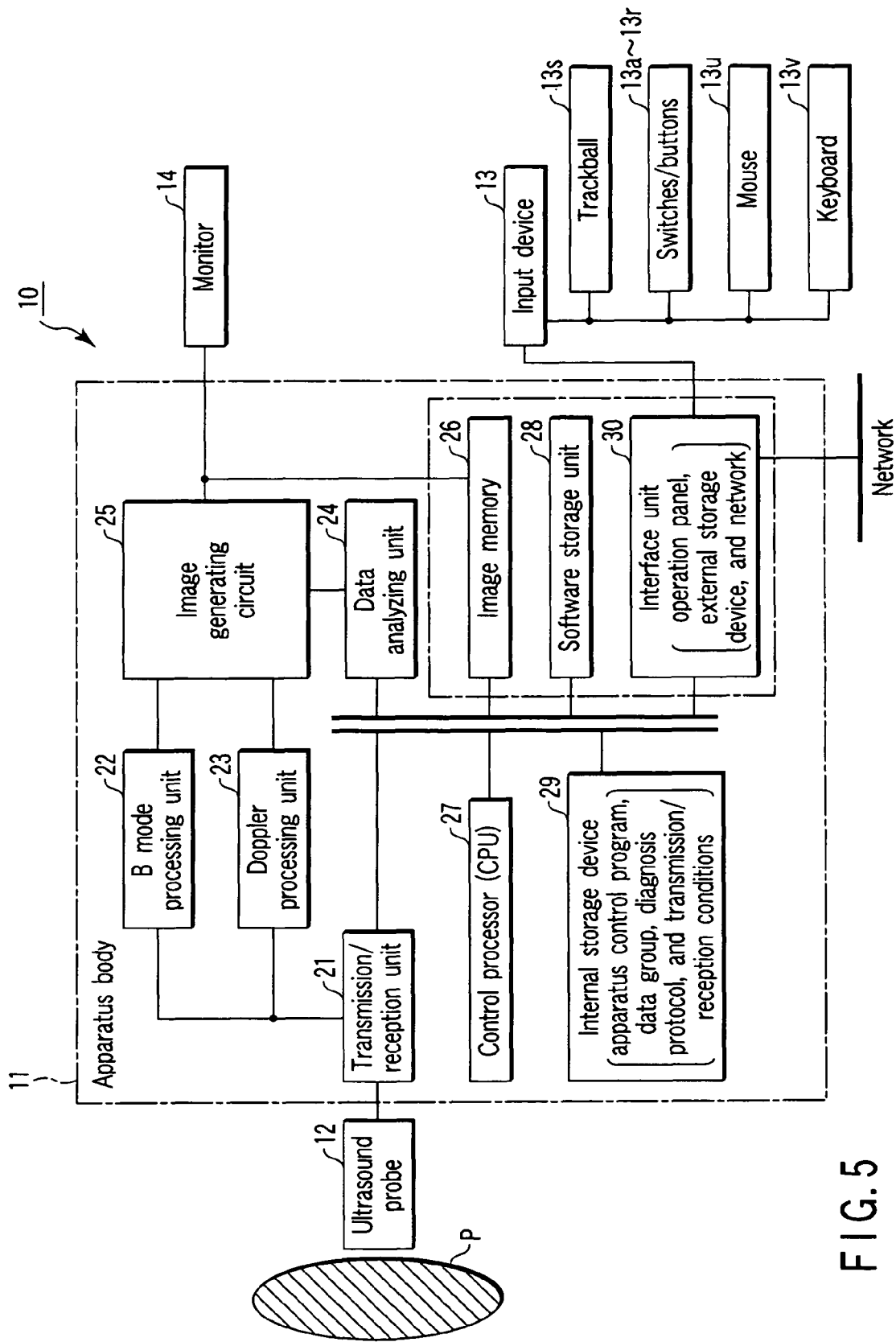
FIG. 5 is a block diagram showing the arrangement of an ultrasound diagnostic apparatus 10 according to the first embodiment.

FIG. 5 is a block diagram showing the arrangement of an ultrasound diagnostic apparatus 10 according to this embodiment. As shown in FIG. 5, the ultrasound diagnostic apparatus 10 comprises an ultrasound probe 12, input device 13, monitor 14, transmission/reception unit 21, B mode processing unit 22, Doppler processing unit 23, data analyzing unit 24, image generating circuit 25, image memory 26, control processor 27, storage unit 28, and interface unit 30. The function of each constituent element will be described below.

The ultrasound probe 12 includes a plurality of piezoelectric transducers which generate ultrasound waves on the basis of driving signals from the transmission/reception unit 21 and convert reflected waves from a subject to be examined into electrical signals, a matching layer provided for the piezoelectric transducers, a backing member which prevents ultrasound waves from propagating backward from the piezoelectric transducers, and the like. When an ultrasound wave is transmitted from the ultrasound probe 12 to a subject P to be examined, the transmitted ultrasound wave is sequentially reflected by a discontinuity surface of acoustic impedance of internal body tissue, and is received as an echo signal by the ultrasound probe 12. The amplitude of this echo signal depends on an acoustic impedance difference on the discontinuity surface by which the echo signal is reflected. The echo produced when an ultrasound pulse is reflected by the surface of a moving blood flow, cardiac wall, or the like is subjected to a frequency shift depending on the velocity component of the moving body due to a Doppler effect.

The input device 13 is connected to an apparatus body 11 and includes various kinds of switches/buttons 13a, a trackball 13b, a mouse 13c, a keyboard 13d, and the like which are used by an operator to input instructions to set and change various kinds of parameter conditions, an instruction to set a region of interest (ROI), and the like to the apparatus body 11.

The monitor 14 displays morphological information and blood flow information in a living body as images on the basis of video signals from the image generating circuit 25.

The transmission/reception unit 21 includes a trigger generating circuit, delay circuit, and pulser circuit, and the like (none of which are shown). The pulser circuit repeatedly generates rate pulses for the formation of transmission ultrasound waves at a predetermined rate frequency fr Hz (period: 1/fr sec). The delay circuit assigns each rate pulse a delay time necessary for focusing an ultrasound wave into the form of a beam for each channel and determining transmission directivity. The trigger generating circuit applies a driving pulse to the ultrasound probe 12 at the timing based on this rate pulse.

The transmission/reception unit 21 includes an amplifier circuit, A/D converter, adder, and the like (not shown). The amplifier circuit amplifies an echo signal captured through the probe 12 for each channel. The A/D converter assigns the amplified echo signal a delay time necessary for determining reception directivity. The adder then performs addition processing. With this addition, a reflection component is enhanced from a direction corresponding to the reception directivity of the echo signal to form a composite beam for ultrasound transmission/reception in accordance with reception directivity and transmission directivity.

The B mode processing unit 22 receives an echo signal from the transmission/reception unit 21, and performs logarithmic amplification, envelope detection processing, and the like for the signal to generate B mode information by which the intensity of the signal is expressed in luminance. This B mode information is transmitted to the image generating circuit 25 and displayed on the monitor 14 as a B mode image representing the intensity of the reflected wave in luminance.

The Doppler processing unit 23 frequency-analyzes velocity information from the echo signal received from the transmission/reception unit 21, extracts a blood flow or tissue owing to a Doppler effect and a contrast medium echo component, and obtains blood information such as mean velocities, variances, powers, and the like at multiple points. The obtained blood flow information is sent as Doppler information to the image generating circuit 25, and is displayed in color as an mean velocity image, a variance image, a power image, and a combined image thereof on the monitor 14.

The data analyzing unit 24 executes quantitative analysis processing on the basis of the B mode information received from the B mode processing unit 22 or the Doppler information received from the Doppler processing unit 23. Quantitative analysis processing includes processing of generating a TIC (Time Intensity Curve) plotting a temporal change in luminance information by using B mode information, and blood flow information measurement processing of obtaining quantitative blood flow indexes such as a PI, RI, and S/D by using Doppler information.

Note that the PI, RI, and S/D which are pieces of typical blood flow information are defined as follows:

$$PI = (V\text{max} - V\text{min}) / V\text{mean} \quad (1)$$

$$RI = (V\text{max} - V\text{min}) / V\text{max} \quad (2)$$

$$S/D = V\text{max} / V\text{ed} \quad (3)$$

where Vmax is the maximum value of blood flow velocity, Vmin is the minimum value of blood flow velocity, Vmean the mean value of blood flow velocities, and Ved is the blood flow velocity at end-diastolic.

The above blood flow information measurement is executed by using the Doppler waveform obtained by an automatic tracing process in the tracing direction. The data analyzing unit 24 has an automatic tracing direction determining function of automatically determining a tracing direction for this automatic tracing process. This function will be described later in detail.

The image generating circuit 25 includes a signal processing circuit, scan converter, and image formatter (none of which are shown). The signal processing circuit performs filtering so as to determine an image quality at the level of a scanning line signal string for ultrasound scanning operation. An output from the signal processing circuit is sent to the scan converter and at the same time is stored in the image memory 26. The scan converter converts the scanning line signal string for ultrasound scanning operation into a scanning line signal string in a general video format typified by a TV format. This output is sent to the image formatter, in which the output is combined with image processing such as adjustment of a luminance and contrast and spatial filtering, character information of various setting parameters, a scale, and the first or second reference line (to be described later). The resultant signal is output as a video signal to the monitor 14. The image formatter controls the position of a baseline displayed on the monitor 14, a Doppler waveform display scale, and the like in response to predetermined operation with the input device 13.

The image memory 26 comprises a storage memory which stores image data received from the image generating circuit 25. This image data can be read out by the operator after, for example, diagnosis, and can be played back as a still image or as a moving image using a plurality of frames.

The control processor 27 has a function as an information processing apparatus (computer) and statically or dynamically controls the operation of the ultrasound diagnostic apparatus body.

The interface unit 30 is an interface concerning the input device 13, a network, and a new external storage device (not shown). Data such as an ultrasound image and an analysis result obtained by this apparatus can be transferred to another apparatus by the interface unit 30 through the network.

(Automatic Tracing Direction Determining Function)

The automatic tracing direction determining function executed by the data analyzing unit 24 will be described in detail next. This automatic tracing direction determining function serves to automatically determine a tracing direction in accordance with the first reference line for controlling the Doppler waveform display scale and the second reference line whose position can be arbitrarily set by the operator. For the sake of simplicity, assume that the first reference line is a Doppler waveform display baseline (a line indicating blood flow velocity=0), and the second reference line is a straight line (midline) which vertically (in the longitudinal axis direction) divides a Doppler waveform display area into halves.

Figure 6:
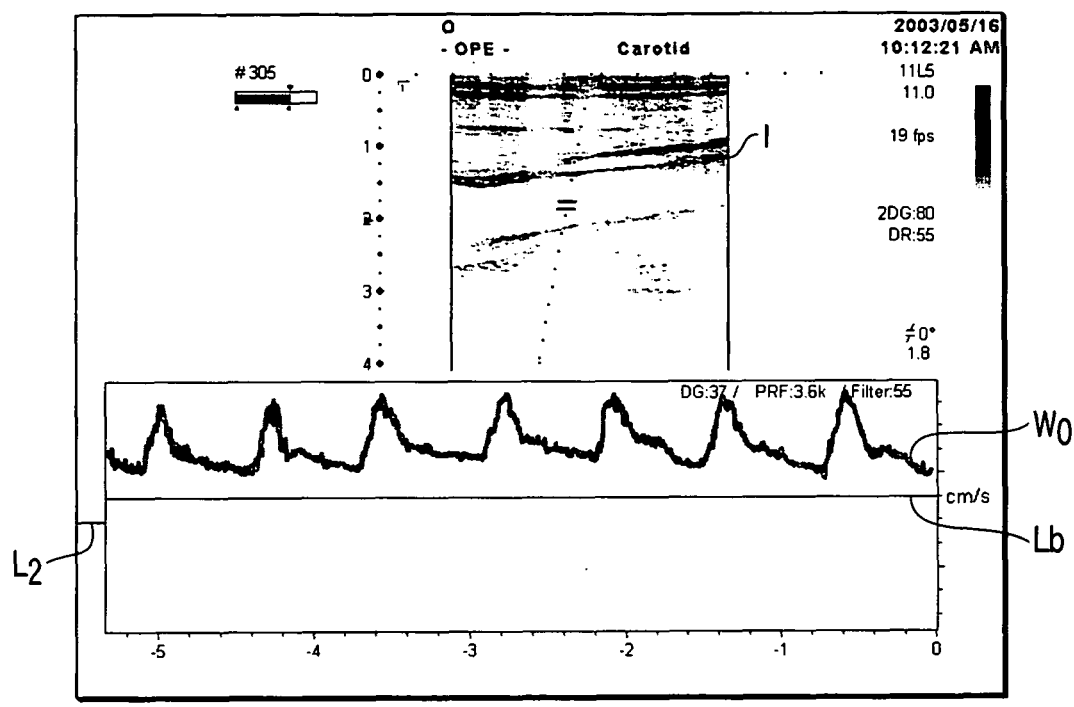
FIG. 6 is a view showing an ultrasound image I indicating a Doppler waveform W, a baseline Lb, a second reference line L2, and a scan area to be scanned in a Doppler mode, which are displayed on a monitor 14.

FIG. 6 shows a Doppler waveform Wo, a baseline Lb, a second reference line L2, and an ultrasound image I indicating a scan area in the Doppler mode, which are displayed on the monitor 14. FIG. 6 shows an example in which the second reference line is displayed. However, this line can be hidden by setting as needed.

Figure 7:
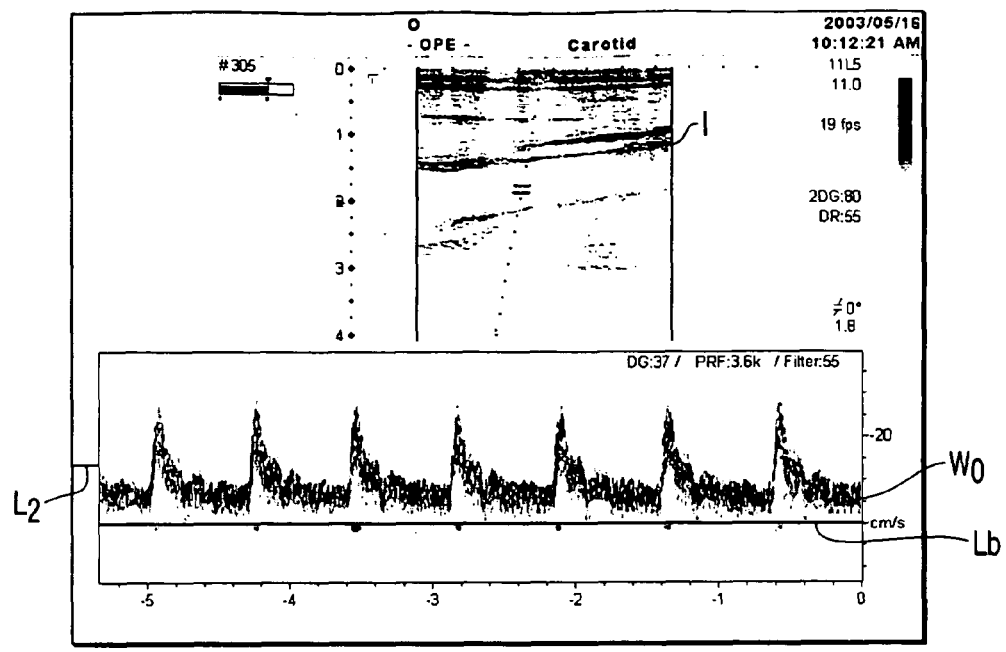
FIG. 7 is a view showing a monitor window in FIG. 2 after the display scale of a Doppler waveform is changed.

The Doppler waveform shown in the example of FIG. 6 appears frequently on the upper side of the second reference line L2. In such a case, in order to allow the Doppler waveform to be observed more easily, the operator moves the baseline Lb downward by manual or automatic operation and changes the Doppler waveform display scale as shown in FIG. 7.

Figure 8:
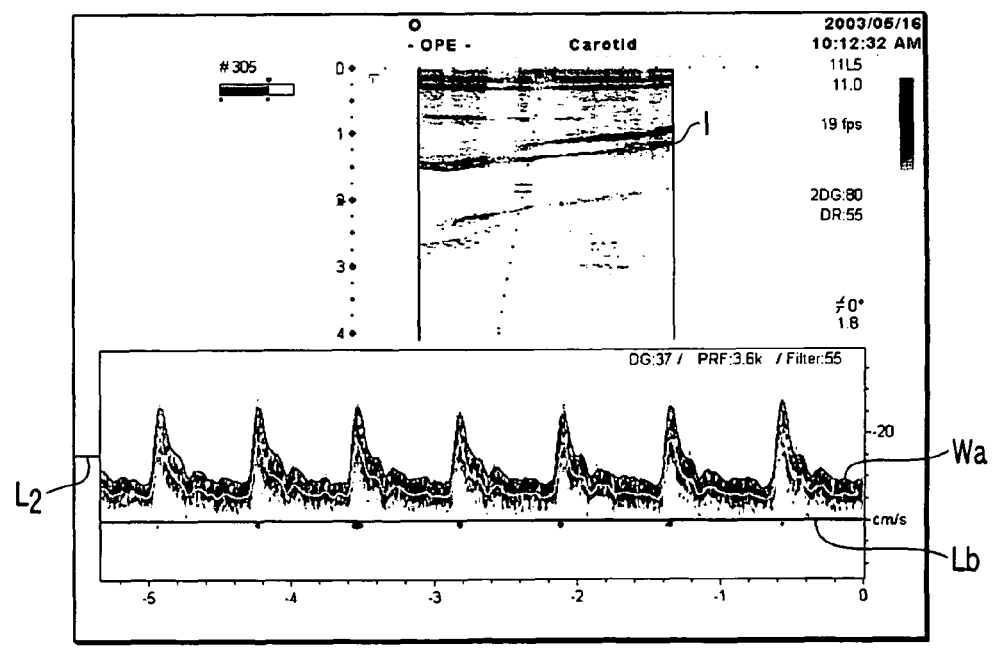
FIG. 8 is a view showing a monitor window including a Doppler waveform having undergone an automatic tracing process.

When the position of the baseline Lb is determined (i.e., a Doppler waveform display scale is determined), the data analyzing unit 24 detects that the position of the baseline Lb is located below the second reference line L2, and executes an automatic tracing process upon regarding a direction above the baseline Lb (the forward direction, i.e., the blood flow direction toward the probe) as a tracing direction, as shown in FIG. 8. The reason why the tracing direction is set to the forward direction when the position of the baseline Lb is located below the second reference line L2 is that a display scale is determined to set a wide display area above the baseline Lb, and it is thought that many portions of the Doppler waveform appear on the upper side (forward direction) of the baseline Lb.

Figure 9:
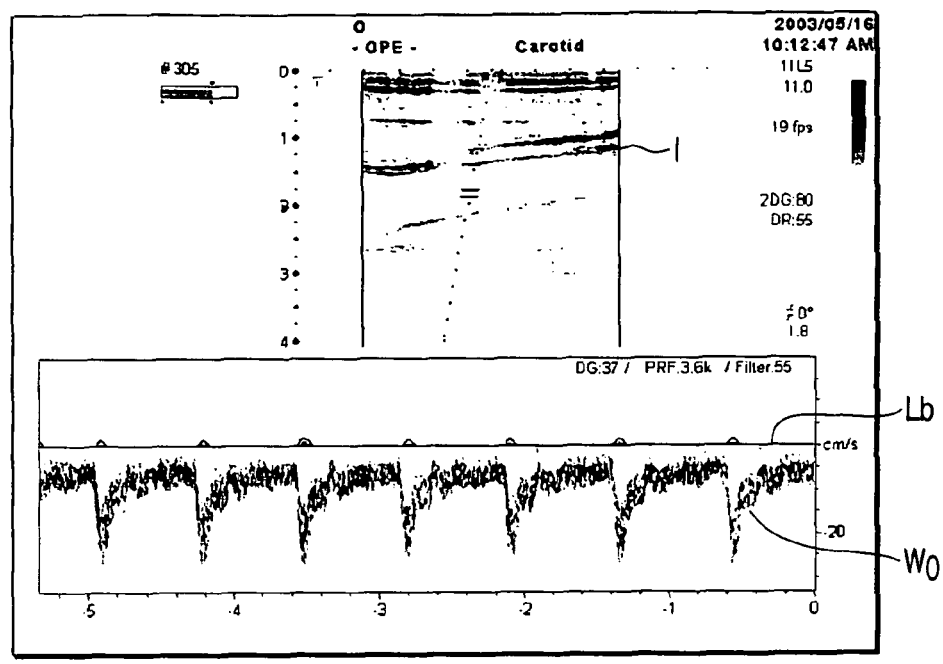
FIG. 9 is a view showing a monitor window when a baseline is set on the upper side of the second reference line.
Figure 10:
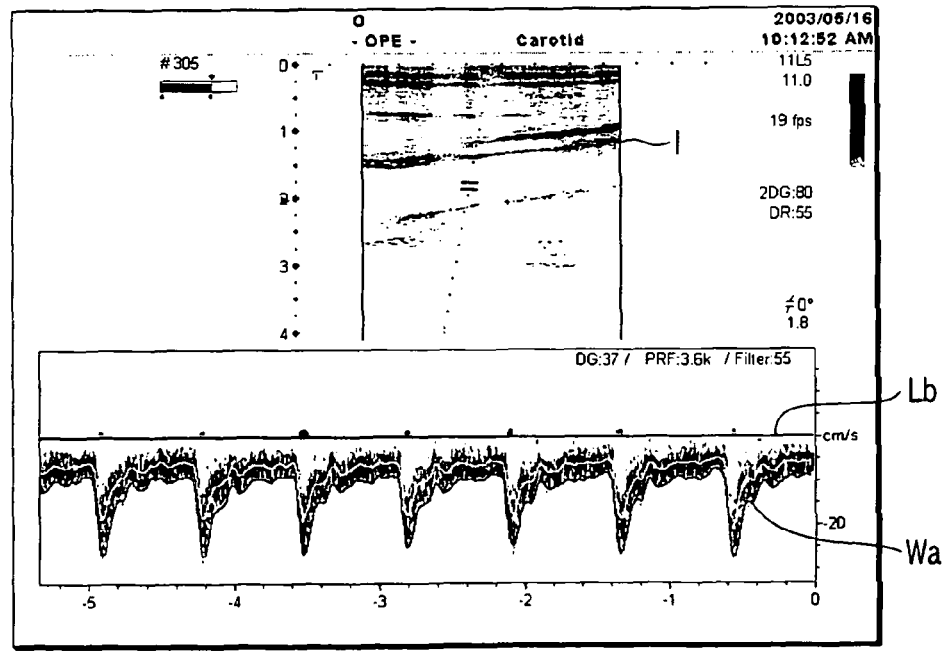
FIG. 10 is a view for explaining an automatic tracing process when the baseline is set on the upper side of the second reference line.

When the position of the baseline Lb is set above the second reference line L2 as shown in FIG. 9, the data analyzing unit 24 executes an automatic tracing process upon regarding the downward direction from the baseline Lb (reverse direction, i.e., the blood flow direction toward the probe) as a tracing direction, as shown in FIG. 10, in accordance with the positional relationship between the baseline Lb and the second reference line L2. The reason why the tracing direction is set to the reverse direction when the position of the baseline Lb is located below the second reference line L2 is that a display scale is determined to set a wide display area below the baseline Lb, and it is thought that many portions of the Doppler waveform appear on the lower side (reverse direction) of the baseline Lb.

In the above case, the first reference line is the baseline Lb, and the second reference line is the straight line vertically dividing the Doppler waveform display area into halves. However, the present invention need not be limited to this, and a desired straight line parallel to the abscissa of the Doppler waveform display area can be selected as each reference line.

Figure 11:
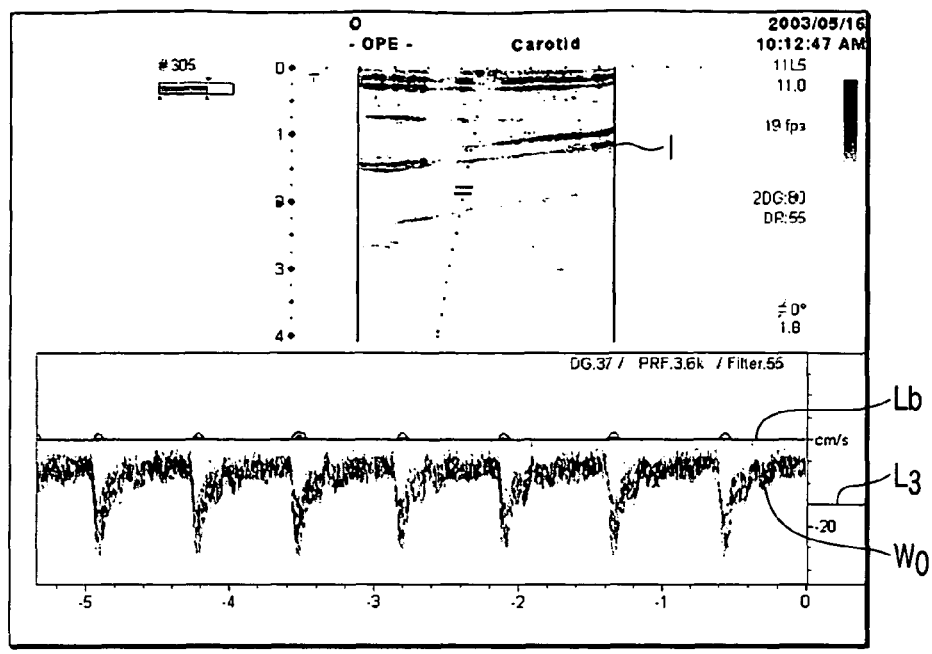
FIG. 11 is a view showing a case wherein a straight line L3 located below a straight line vertically dividing a Doppler waveform display area into halves by a predetermined amount is selected as the second reference line.
Figure 12:
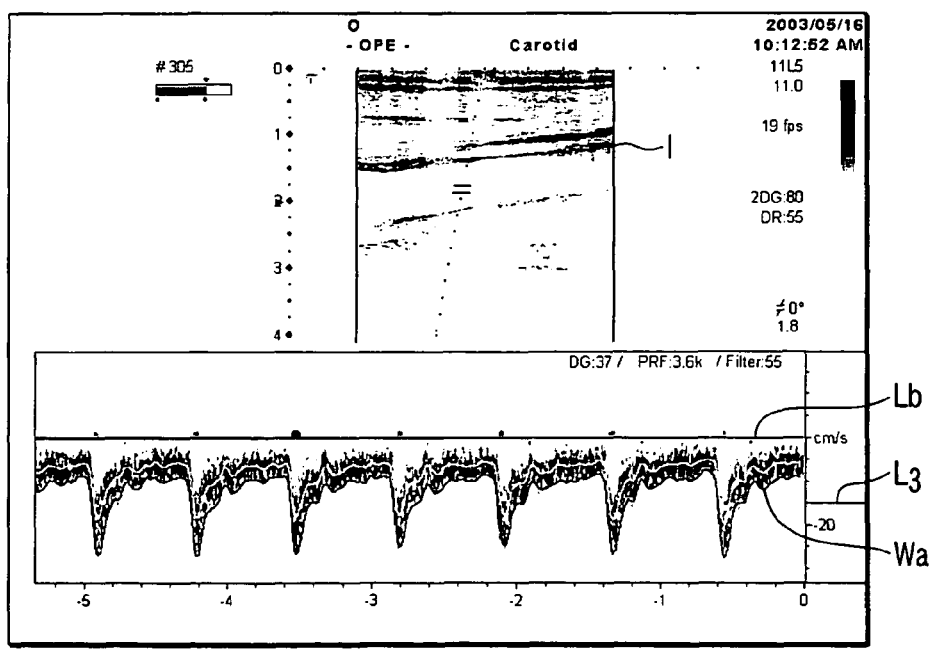
FIG. 12 is a view showing a monitor window including a Doppler waveform obtained by performing an automatic tracing process with respect to the case shown in FIG. 11.

FIG. 11 is a view showing an example in which a straight line L3 located below the straight line vertically dividing the Doppler waveform display area into halves by a predetermined amount is selected as the second reference line. In such a case as well, the data analyzing unit 24 determines a tracing direction by performing the above determination on the basis of the positional relationship between the first and second reference lines, and executes an automatic tracing process in the determined direction, as shown in FIG. 12.

(Modification 1)

A modification of this automatic tracing direction determining function will be described next. The automatic tracing direction determining function according to this modification serves to automatically determine a tracing direction on the basis of whether the first reference line is located in a range (reference range) set in advance on the upper side of the Doppler waveform display coordinate system.

Figure 13:
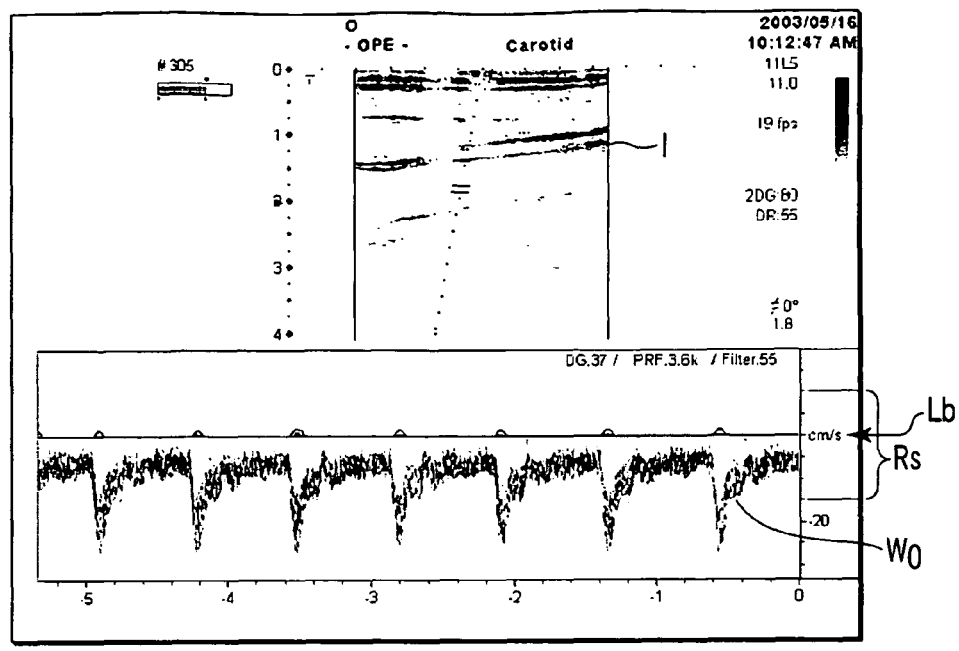
FIG. 13 is a view showing an example of a reference range Rs set in a Doppler waveform display area.

FIG. 13 is a view showing an example of a reference range Rs set in the Doppler waveform display area. Note that the reference range Rs can also be displayed in a predetermined form or hidden by setting as needed.

Figure 14:
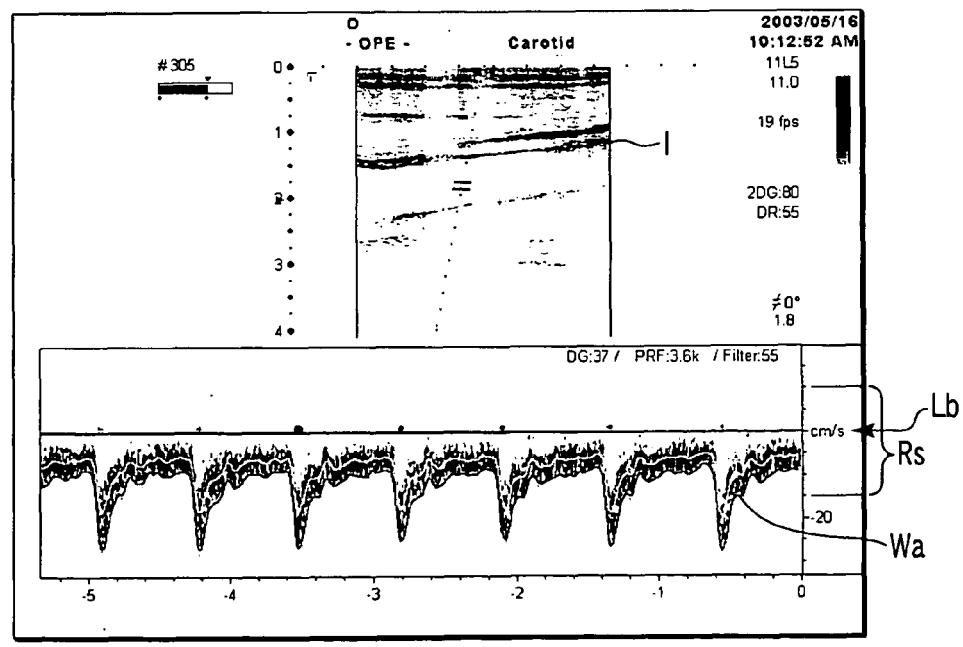
FIG. 14 is a view for explaining an automatic tracing process when the baseline is located in the reference range Rs.

As shown in FIG. 13, the baseline Lb as the first reference line is located in the reference range Rs. Upon detecting that the baseline Lb is located in the reference range Rs, the data analyzing unit 24 determines that many portions of a Doppler waveform appear on the lower side (in reverse direction) of the baseline Lb, and determines the reverse direction as a tracing direction, as shown in FIG. 14. The data analyzing unit 24 then executes an automatic tracing process.

If the baseline Lb is located outside the reference range Rs, the data analyzing unit 24 determines that many portions of the Doppler waveform appear on the upper side (in the forward direction) of the baseline Lb, and determines the forward direction as a tracing direction. The data analyzing unit 24 then executes an automatic tracing process.

Note that the position of the reference range Rs can be arbitrarily set. Therefore, for example, in contrast to the example shown in FIGS. 13 and 14, an area can be set below the Doppler waveform display coordinate system.

This modification can be regarded as a technique of setting two boundary lines of the reference range Rs as the second reference lines described above and determining a tracing direction in accordance with the positional relationship between the two lines and the baseline Lb.

(Modification 2)

Another modification of this automatic tracing direction determining function will be described next. When a mask area (an area excluded from an automatic tracing process target area) is set in a Doppler waveform display area, the automatic tracing direction determining function according to another modification executes automatic tracing direction determining operation according to the above embodiment or modification 1 in the Doppler waveform display area (automatic tracing process target area) excluding the mask area. The function according to this modification is effective when, for example, only one piece of blood flow information is to be extracted and other pieces of blood flow information are to be excluded in, for example, quantitative analysis on a region where blood flows in opposite directions are intricately arranged, like umbilical cord blood flows.

Figure 15:
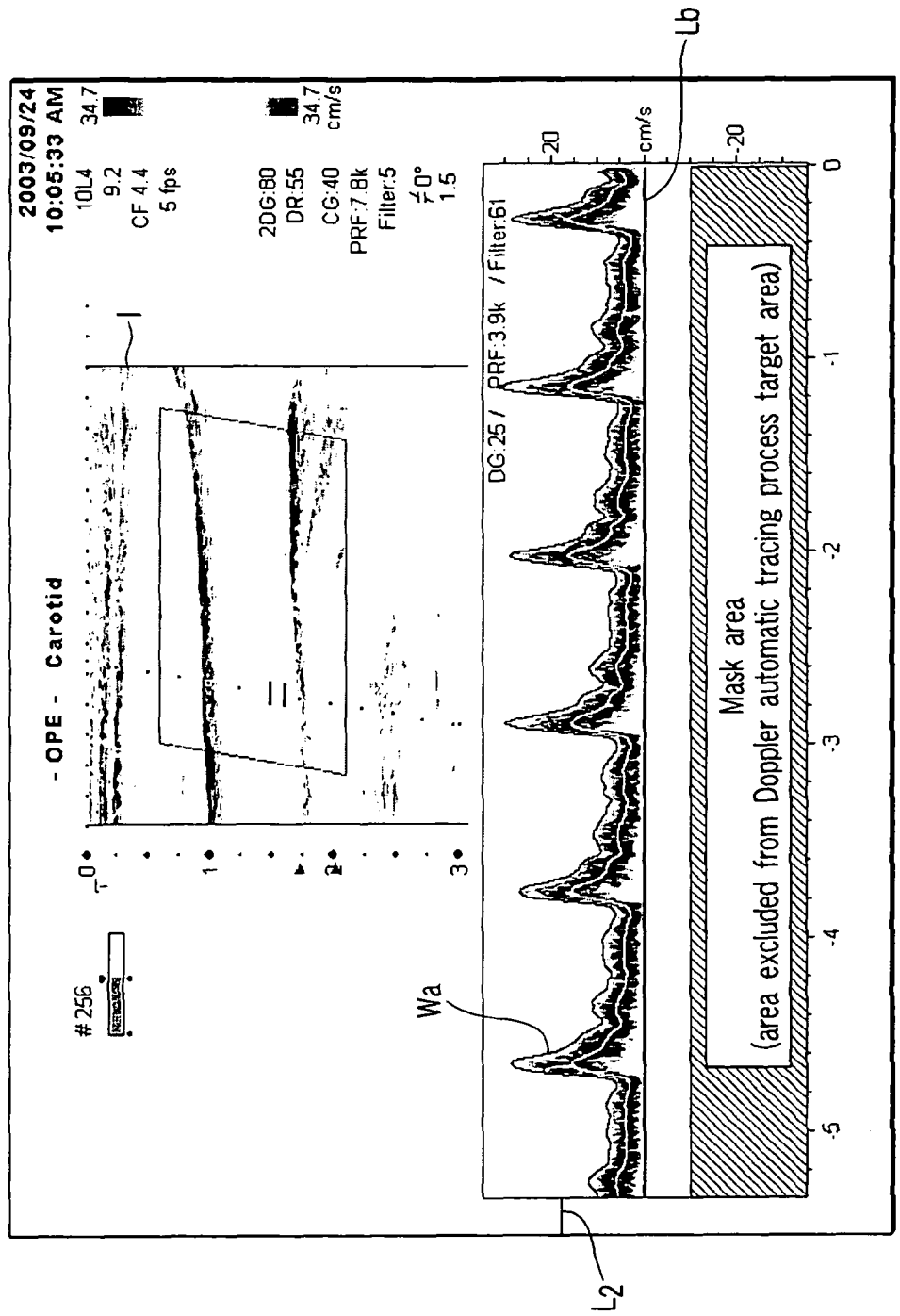
FIG. 15 is a view showing a view for explaining an automatic tracing direction determining function according to a modification and, more specifically, a view showing an example of a monitor window in which a mask area is set in a Doppler waveform display area.

FIG. 15 is a view for explaining the automatic tracing direction determining function according to this modification and, more specifically, a view showing an example of monitor window in which a mask area is set in a Doppler waveform display area. Referring to FIG. 15, the position of the second reference line is newly set in the automatic tracing process target area, and the position of the baseline Lb is further determined. The data analyzing unit 24 determines a tracing direction on the basis of the positional relationship between the second reference line in this automatic tracing process target area and the baseline Lb, and executes an automatic tracing process concerning the determined tracing direction.

Note that from the viewpoint of workability, it is preferable to inhibit setting of the second reference line, first reference line, and baseline Lb in a mask area.

(Operation)

Figure 16:
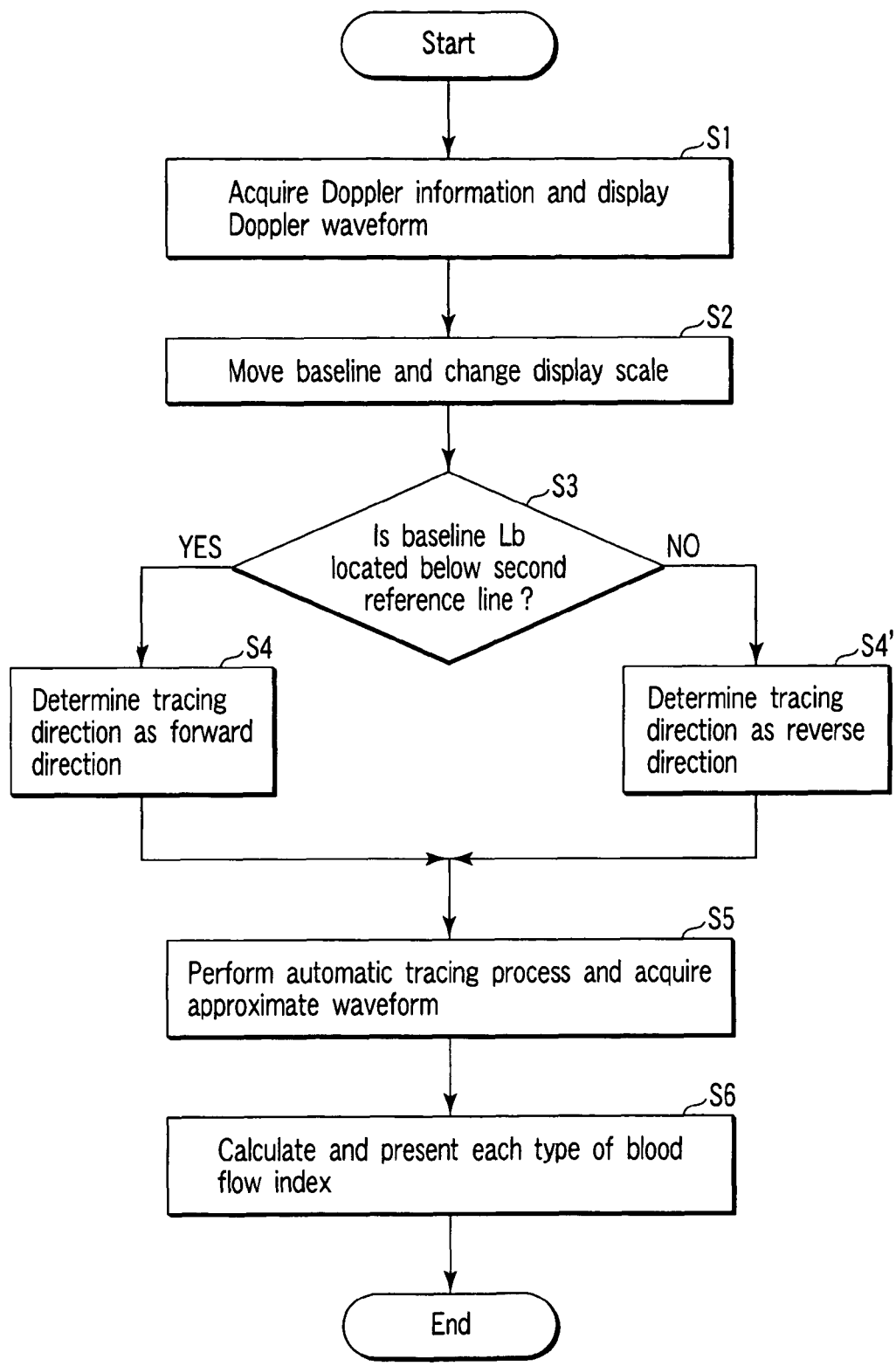
FIG. 16 is a flowchart showing the flow of each process to be executed in blood flow information measuring processing.

The operation of blood flow information measurement processing by the ultrasound diagnostic apparatus 10 will be described with reference to FIG. 16. FIG. 16 is a flowchart showing the flow of each process executed in blood flow information measurement processing.

As shown in FIG. 16, first of all, Doppler information is acquired by imaging based on a predetermined sequence, and a Doppler waveform is displayed on the monitor 14 in a predetermined scale (step S1). In response to an instruction to move the baseline of the Doppler waveform displayed on the monitor, the image generating circuit 25 changes the scale of the Doppler waveform displayed on the monitor 14 (step S2).

The data analyzing unit 24 determines the positional relationship between the baseline set in step S2 and the second reference line set in advance (step S3). If it is determined that the baseline is located below the second reference line, the forward direction is determined as a tracing direction (step S4). If it is determined that the baseline is located above the second reference line, the reverse direction is determined as a tracing direction (step S4').

The data analyzing unit 24 acquires an approximate value of the Doppler waveform by executing an automatic tracing process concerning the tracing direction determined in step S4 or S4' (step S5), and calculates each type of quantitative value by using this approximate value. Each type of quantitative value calculated here is displayed on the monitor in a predetermined form and presented to the operator (step S6).

According to the above arrangement, the following effects can be obtained.

According to this ultrasound diagnostic apparatus, a tracing direction in an automatic tracing process can be automatically determined in accordance with the positional relationship between the first reference line for determining a Doppler waveform display scale and the second reference line set in advance at a desired position or whether the first reference line is located in a reference range set in advance at a desired position. This makes it possible to execute an automatic tracing process in a proper tracing direction without artificially determining any tracing direction in blood flow information measurement processing. Therefore, the efficiency of overall work can be improved, thereby reducing the mental and physical strains on the operator and subject.

In addition, according to this ultrasound diagnostic apparatus, even if a mask area is set in a Doppler waveform display area, a tracing direction in an automatic tracing process can be automatically determined in accordance with, for example, the positional relationship between the first and second reference lines in an automatic tracing process target area with the mask area being excluded from the Doppler waveform display area. Even if, therefore, blood flow information measurement is to be performed with attention being paid to only a specific blood flow velocity, the same effects as described above can be obtained.

Second Embodiment

The second embodiment of the present invention will be described next. An ultrasound diagnostic apparatus according to this embodiment has an automatic analysis target discriminating function. The apparatus of the first embodiment is designed to automatically determine (automatic tracing direction determining function) a tracing direction before the execution of an automatic tracing process and perform an automatic tracing process and quantitative analysis in the determined tracing direction. In contrast to this, in the second embodiment, after an automatic tracing process is performed in both the forward direction and the reverse direction, it is discriminated, on the basis of the position of a baseline, whether to set Doppler information concerning the forward direction or Doppler information concerning the reverse direction as an analysis target. Quantitative analysis is performed for only an approximate value of a Doppler waveform corresponding to the determined direction, and the result is displayed.

Note that all the techniques described in the first embodiment can be applied to analysis target determination based on the position of a baseline. When, for example, modification 1 or modification 2 described in the first embodiment is to be applied to the second embodiment, determination similar to that described in each modification may be executed in step S14 in FIG. 17. For the sake of concreteness, a case will be exemplified below wherein an analysis target is determined on the basis of the positional relationship between a baseline and a midline.

Figure 17:
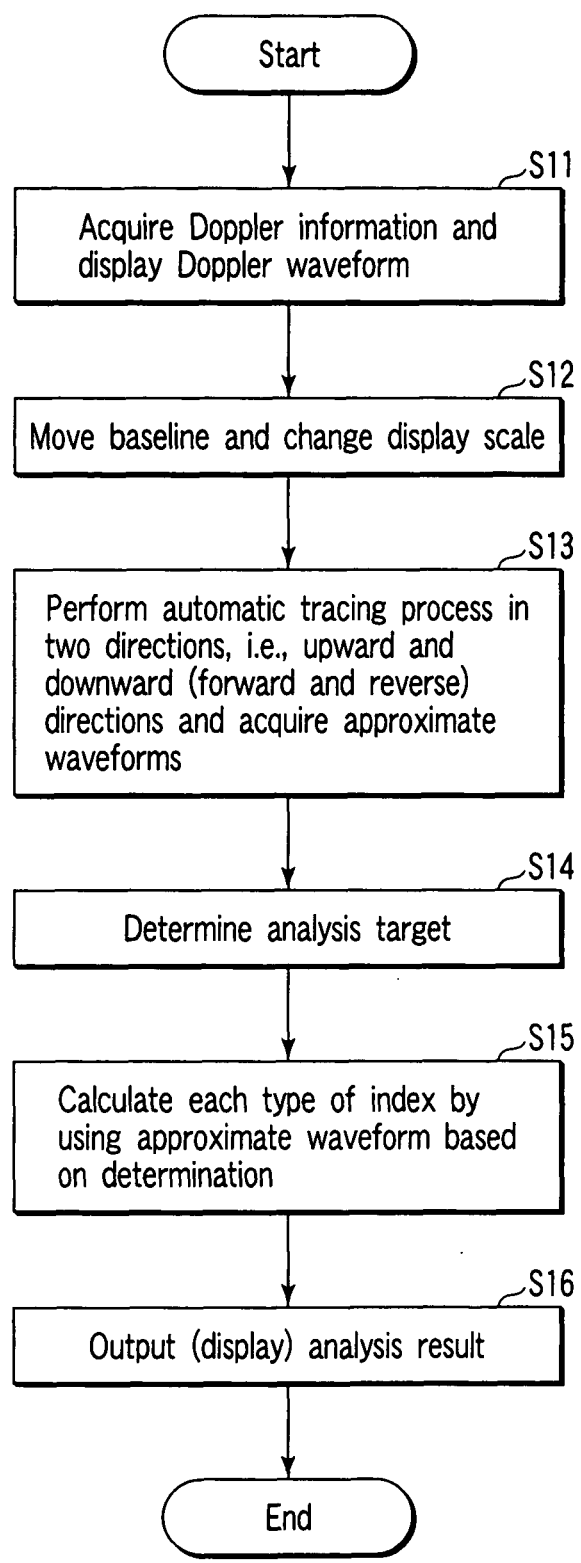
FIG. 17 is a flowchart showing the flow of each process in blood flow information measurement processing by an apparatus according to the second embodiment.

FIG. 17 is a flowchart showing the flow of each process in blood flow information measurement processing by the apparatus according to this embodiment. As shown in FIG. 17, Doppler information is acquired by imaging based on a predetermined sequence, and a Doppler waveform is displayed on a monitor 14 in a predetermined scale (step S11). An image generating circuit 25 changes the scale of the Doppler waveform displayed on the monitor 14 in response to an instruction to move the baseline of the Doppler waveform displayed on the monitor 14 (step S12).

A data analyzing unit 24 executes an automatic tracing process in both the forward direction and the reverse direction, to acquire an approximate value of a Doppler waveform in each direction (step S13).

The data analyzing unit 24 determines the positional relationship between the baseline set in step S2 and the second reference line set in advance. If the baseline is located below the second reference line, the approximate value of the Doppler waveform concerning the forward direction is determined as an analysis target. If the baseline is located above the second reference line, the approximate value of the Doppler waveform concerning the reverse direction is determined as an analysis target (step S14).

The data analyzing unit 24 then calculates each type of quantitative value by using the approximate value of the Doppler waveform which is determined as the analysis target in step S14 (step S15). Each type of quantitative value calculated here is displayed on the monitor in a predetermined form and presented to the operator (step S16).

According to the above arrangement, an approximate value of a Doppler waveform which is to be an analysis target can be determined in accordance with the positional relationship between the first reference line for determining a Doppler waveform display scale and the second reference line set in advance at a desired position or whether the first reference line is located in a reference range set in advance at a desired position. This makes it possible to automatically select an analysis result effective for diagnosis without artificially determining any approximate value of a Doppler waveform as an analysis target in blood flow information measurement processing. Therefore, the efficiency of overall work can be improved, thereby reducing the mental and physical strains on an operator and subject.

Third Embodiment

The third embodiment of the present invention will be described next. An ultrasound diagnostic apparatus according to this embodiment has an automatic display target discriminating function. In this embodiment, after an automatic tracing process is performed in both the forward direction and the reverse direction, quantitative analysis is performed by using an approximate waveform in each direction. It is then discriminated, on the basis of the position of a baseline, whether a display target is the analysis result concerning the forward direction or the analysis result concerning the reverse direction, and only the analysis result corresponding to the determined direction is displayed.

Note that in analysis target determination based on the position of the baseline, all the techniques described in the first embodiment can be used. When, for example, modification 1 or modification 2 described in the first embodiment is to be applied to the third embodiment, determination similar to that described in each modification may be executed in step S25 in FIG. 18. For the sake of concreteness, a case will be exemplified below wherein an analysis target is determined on the basis of the positional relationship between a baseline and a midline.

Figure 18:
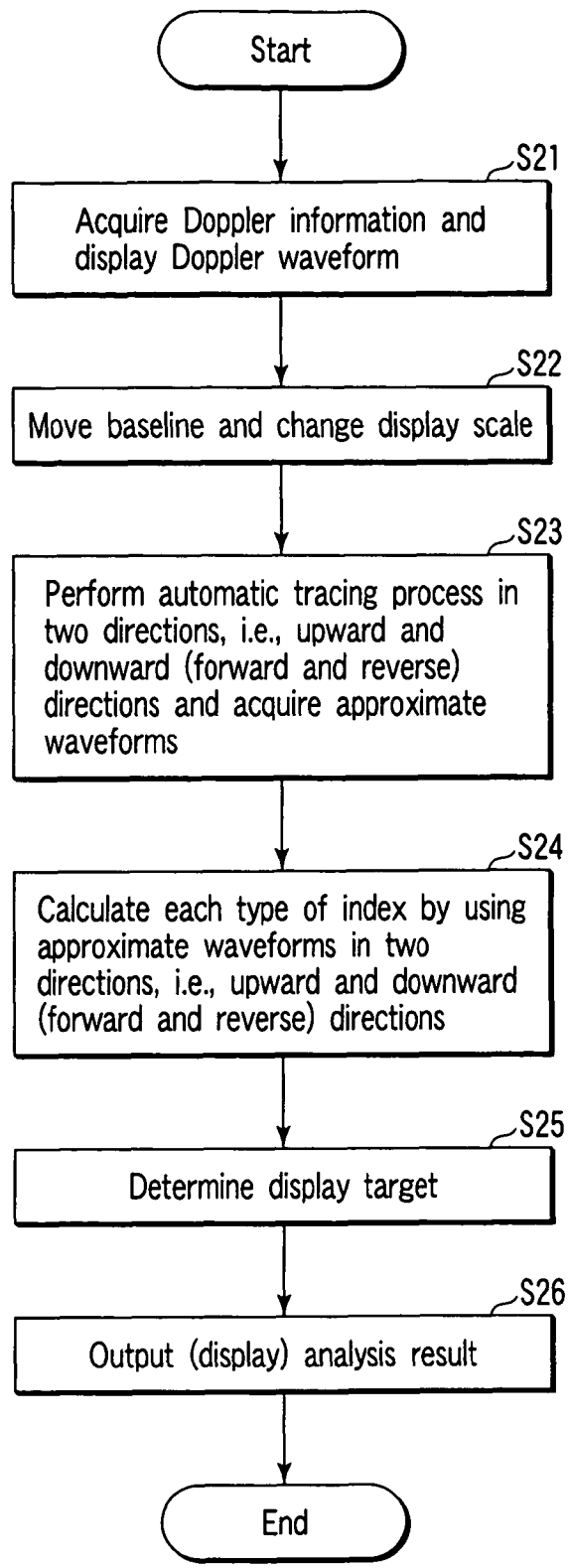
FIG. 18 is a flowchart showing the flow of each process in blood flow information measurement processing by an apparatus according to the third embodiment.

FIG. 18 is a flowchart showing the flow of each process in blood flow information measurement processing by the apparatus according to this embodiment. As shown in FIG. 18, first of all, Doppler information is acquired by imaging based on a predetermined sequence, and a Doppler waveform is displayed on a monitor 14 in a predetermined scale (step S21). An image generating circuit 25 changes the scale of the Doppler waveform displayed on the monitor 14 in response to an instruction to move the baseline of the Doppler waveform displayed on the monitor 14 (step S22).

A data analyzing unit 24 executes an automatic tracing process concerning both the forward direction and the reverse direction, to acquire an approximate value of a Doppler waveform concerning each direction (step S23).

The data analyzing unit 24 calculates each type of quantitative value in each direction by using the acquired approximate value of each Doppler waveform (step S24).

The data analyzing unit 24 determines the positional relationship between the baseline set in step S2 and the second reference line set in advance. If it is determined that the baseline is located below the second reference line, the quantitative value concerning the forward direction is determined as a display target. If the baseline is located above the second reference line, the quantitative value concerning the reverse direction is determined as a display target (step S25). The quantitative value determined as a display target is displayed on the monitor in a predetermined form and presented to the operator (step S26).

According to the above arrangement, an analysis result which is to be display target can be determined in accordance with the positional relationship between the first reference line for determining a Doppler waveform display scale and the second reference line set in advance at a desired position or whether the first reference line is located in a reference range set in advance at a desired position. This makes it possible to automatically select an analysis result effective for diagnosis without artificially determining any analysis result as a display target in blood flow information measurement processing. Therefore, the efficiency of overall work can be improved, thereby reducing the mental and physical strains on an operator and subject.

Note that the present invention is not exactly limited to the above embodiments, and constituent elements can be modified in the execution stage without departing from the spirit and scope of the invention.

(1) For example, the above automatic tracing direction determination processing and blood flow information measurement processing including this can also be implemented by causing an image processing apparatus or ultrasound diagnostic apparatus such as a workstation to develop a program for causing a computer to execute each processing.

(2) In each embodiment described above, one second reference line or one reference range is set in a Doppler waveform coordinate area, and a tracing direction is determined with reference to the positional relationship between the set reference line or reference range and the first reference line (baseline). However, the number of second reference lines and reference ranges which can be set in a coordinate area need not be limited to one, and a plurality of second reference lines and reference ranges may be set in the coordinate area. In such a case, the tracing direction determination processing described in the above embodiments may be executed with respect to each of the second reference lines (or each of the reference ranges) and the first reference line.

(3) In the first embodiment, automatic tracing direction determination by an automatic tracing process has been described. However, waveform extraction is not an essential requirement. For example, when Doppler information which is not limited to a waveform (which is, for example, velocity values acquired at predetermined time intervals instead of a waveform) is to be approximately extracted concerning a predetermined direction in step S5 in FIG. 16, the direction in which approximate information is to be extracted can be automatically determined by the technique described in the above embodiments.

(4) The above embodiments have exemplified the case wherein an approximate waveform extracted by an automatic tracing process is displayed. However, the display of this approximate waveform is not an essential requirement, and it suffices to display a final analysis result.

(5) Each embodiment described above has exemplified the case wherein an analysis result concerning the direction selected on the apparatus side is finally displayed. However, the present invention is not limited to this, and analysis results concerning both the forward direction and the reverse direction may be simultaneously or sequentially displayed.

(6) In each embodiment described above, an analysis result to be displayed may be displayed in the form that allows to determine whether the analysis result concerns the forward or reverse direction. More specifically, for example, character information such as "Forward" or "Reverse" may be displayed together with a Doppler waveform, or an analysis result may be displayed in color, e.g., displaying an analysis result concerning the forward direction in blue and an analysis result concerning the reverse direction in red.

Various inventions can be formed by properly combining a plurality of constituent elements disclosed in the above embodiments. For example, several constituent elements may be omitted from all the constituent elements described in the embodiments. In addition, constituent elements throughout different embodiments may be properly combined.

What is claimed is:

1. An ultrasound diagnostic apparatus comprising:
a computer comprising:
   a Doppler information generating processor which generates blood flow Doppler waveforms concerning at least one of a first direction and second direction on the basis of echo signals obtained by ultrasound waves transmitted to a subject to be examined on the basis of supplied driving signals;
   a determining processor which determines, based on a position of a baseline of the Doppler waveforms within a display area of the Doppler waveforms, said baseline indicating a zero Doppler velocity and set at a position where a Doppler shift is zero, an end portion of the Doppler waveforms in a positive frequency direction or an end portion of the Doppler waveforms in a negative frequency direction as a target region;
   wherein the determining processor sets the target region, depending on whether the baseline is located in a first range set in a display area of the Doppler waveforms, the first range set including the reference line as one of two boundary lines; and
   an approximate information generating processor which generates approximate information by tracing the blood flow Doppler waveforms corresponding to the target region;
   wherein the approximate information generating processor generates approximate waveforms as the approximate information; and
   a display which displays the approximate information in the target region above or below the baseline based on the set target region, and
   wherein the determining processor performs the determination in accordance with a positional relationship between the baseline and a reference line set in advance at a desired position in the display area of the Doppler waveforms, and wherein the reference line indicates the desired position and vertically divides the display area of the Doppler waveforms.

2. An apparatus according to claim 1, wherein when the first direction is a direction toward a transmission source of the transmitted ultrasound wave, and the second direction is a direction away from the transmission source, the determining processor generates approximate information of the blood flow Doppler waveforms above the baseline if the baseline is located below the reference line, and generates approximate information of the blood flow Doppler waveforms below the baseline if the baseline is located above the reference line.

3. An apparatus according to claim 1, which further comprises a changing processor which changes the position of the baseline of the Doppler waveforms in the display area of the Doppler waveforms according to an operation by user, and wherein
   the determining processor performs the determination on the basis of the changed position of the baseline.

4. An apparatus according to claim 1, which further comprises a changing processor which changes the first range, and in which
   the determining processor performs the determination by using the first range after the change made by the changing processor.

5. An apparatus according to claim 1, which further comprises a setting processor which sets, in the display area of the Doppler waveforms, an inhibition area which inhibits movement and setting of the baseline and generation of approximate information of the blood flow Doppler waveforms, and in which
   the determining processor executes the determination in accordance with a position of the baseline set outside the inhibition area.

6. An apparatus according to claim 1, wherein
   the approximate information generating processor generates the approximate information concerning both the first direction and the second direction.

7. An apparatus according to claim 6, wherein
   when the first direction is a direction toward a transmission source of the transmitted ultrasound wave, and the second direction is a direction away from the transmission source, the determining processor generates approximate information of the blood flow Doppler waveforms above the baseline if the baseline is located below the reference line, and generates approximate information of the blood flow Doppler waveforms below the baseline if the baseline is located above the reference line.

8. An apparatus according to claim 6, which further comprises a changing processor which changes the position of the baseline of the Doppler waveforms in the display area of the Doppler waveforms according to an operation by user, and wherein
   the determining processor performs the determination on the basis of the changed position of the baseline.

9. An apparatus according to claim 6, wherein the determining processor sets the target region, depending on whether the baseline is located in a first range set in a display area of the Doppler waveforms, the first range set including the reference line as one of two boundary lines.

10. An apparatus according to claim 9, which further comprises a changing processor which changes the first range, and in which
   the determining processor performs the determination by using the first range after the change made by the changing processor.

11. An apparatus according to claim 6, which further comprises a setting processor which sets, in the display area of the Doppler waveforms, an inhibition area which inhibits movement and setting of the baseline and generation of approximate information of the blood flow Doppler waveforms, and in which
    the determining processor executes the determination in accordance with a position of the baseline set outside the inhibition area.

12. An apparatus according to claim 6, wherein the display displays the baseline in a predetermined form.

13. An apparatus according to claim 1, wherein
    the approximate information generating processor generates the approximate information concerning both the first direction and the second direction, and
    the display displays the approximate information concerning the direction determined by the determining processor.

14. An apparatus according to claim 13, wherein
    when the first direction is a direction toward a transmission source of the transmitted ultrasound wave, and the second direction is a direction away from the transmission source, the determining processor generates approximate information of the blood flow Doppler waveforms above the baseline if the baseline is located below the reference line, and generates approximate information of the blood flow Doppler waveforms below the baseline if the baseline is located above the reference line.

15. An apparatus according to claim 13, which further comprises a changing processor which changes the position of the baseline of the Doppler waveforms in the display area of the Doppler waveforms according to an operation by user, and wherein
    the determining processor performs the determination on the basis of the changed position of the baseline.

16. An apparatus according to claim 13, wherein the determining processor sets the target region, depending on whether the baseline is located in a first range set in the display area of the Doppler waveforms, the first range set including the reference line as one of two boundary lines.

17. An apparatus according to claim 16, which further comprises a changing processor which changes the first range, and in which
    the determining processor performs the determination by using the first range after the change made by the changing processor.

18. An apparatus according to claim 13, which further comprises a setting processor which sets, in the display area of the Doppler waveforms, an inhibition area which inhibits movement and setting of the baseline and generation of approximate information of the blood flow Doppler waveforms, and in which
    the determining processor executes the determination in accordance with a position of the baseline set outside the inhibition area.

19. An apparatus according to claim 1, further comprising:
    a changing processor which changes the position of the baseline of the Doppler waveforms in the display area of the Doppler waveforms according to an operation by user, and wherein the determining processor performs determination on the basis of the changed position of the baseline.

20. An ultrasound signal analyzing method comprising:
    generating blood flow Doppler waveforms concerning at least one of a first direction and second direction on the basis of an echo signal obtained by an ultrasound wave transmitted to a subject to be examined on the basis of a supplied driving signal;
    determining, based on a position of a baseline of the Doppler waveforms within a display area of the Doppler waveforms, said baseline indicating a zero Doppler velocity and set at a position where a Doppler shift is zero, an end portion of the Doppler waveforms in a positive frequency direction or an end portion of the Doppler waveforms in a negative frequency direction as a target region;
    setting the target region, depending on whether the baseline is located in a first range set in a display area of the Doppler waveforms, the first range set including the reference line as one of two boundary lines;
    generating approximate information by tracing the blood flow Doppler waveforms corresponding to the target region;
    generating the approximate waveforms as the approximate information; and
    displaying the approximate information in the target region above or below the baseline based on the set target region, and
    wherein the determining includes performing the determination in accordance with a positional relationship between the baseline and a reference line set in advance at a desired position in the display area of the Doppler waveforms, and
    wherein the reference line indicates the desired position which vertically divides the display area of the Doppler waveforms.

* * * * *